(12) United States Patent
Vartiainen et al.

(10) Patent No.: US 10,869,789 B2
(45) Date of Patent: Dec. 22, 2020

(54) DISPOSABLE ABSORBENT PRODUCTS IN A STACKED ARRANGEMENT

(71) Applicant: Essity Hygiene and Health Aktiebolag, Gothenburg (SE)

(72) Inventors: Kent Vartiainen, Lerum (SE); Elisabeth N. Lundin, Mölnlycke (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 459 days.

(21) Appl. No.: 14/774,885

(22) PCT Filed: Mar. 14, 2013

(86) PCT No.: PCT/SE2013/050242
§ 371 (c)(1),
(2) Date: Sep. 11, 2015

(87) PCT Pub. No.: WO2014/142720
PCT Pub. Date: Sep. 18, 2014

(65) Prior Publication Data
US 2016/0015577 A1 Jan. 21, 2016

(51) Int. Cl.
*A61F 13/20* (2006.01)
*A61F 13/551* (2006.01)

(52) U.S. Cl.
CPC .............................. *A61F 13/55115* (2013.01)

(58) Field of Classification Search
CPC .............. A61F 13/551; A61F 13/55105; A61F 13/55115; A61F 13/42; A61F 13/84; A61F 13/5513; A61F 13/505; A61F 13/44
See application file for complete search history.

(56) References Cited

U.S. PATENT DOCUMENTS

| 5,934,470 A | 8/1999 | Bauer et al. |
| 6,089,368 A | 7/2000 | Lindgren et al. |

(Continued)

FOREIGN PATENT DOCUMENTS

| CN | 1558861 A | 12/2004 | |
| EP | 0 780 325 A1 * | 6/1997 | ............. B65D 85/16 |

(Continued)

OTHER PUBLICATIONS

Japanese Office Action dated Sep. 26, 2016 issued in corresponding Japanese patent application No. 2015-562963 (7 pages).

(Continued)

*Primary Examiner* — Michele M Kidwell
(74) *Attorney, Agent, or Firm* — Faegre Drinker Biddle & Reath LLP

(57) ABSTRACT

Disposable absorbent products are stacked along a stacking axis. Each of a first plurality of folded disposable absorbent products is folded into at least two panels so as to define first and second ends and front and back oppositely-facing exterior faces of each of the first plurality of folded products, with the respective front faces of the first plurality of folded products facing a common, first direction. At least one folded disposable absorbent product is folded substantially in the same manner as the first plurality of folded products to thereby define first and second ends and front and back oppositely-facing exterior faces of that at least one folded product, with the front face of that at least one folded product facing a second direction opposite from the first direction.

23 Claims, 6 Drawing Sheets

(56) References Cited

U.S. PATENT DOCUMENTS

| | | | |
|---|---|---|---|
| 6,097,297 A * | 8/2000 | Fard | A61F 13/42 128/886 |
| 7,250,547 B1 | 7/2007 | Hofmeister et al. | |
| 7,977,529 B2 | 7/2011 | Bergman et al. | |
| 2003/0155265 A1 | 8/2003 | Tippey | |
| 2004/0064122 A1 | 4/2004 | Hansson | |
| 2004/0134822 A1 * | 7/2004 | Otsubo | A61F 13/49001 206/440 |
| 2004/0195137 A1 | 10/2004 | Otsubo | |
| 2005/0156744 A1 | 7/2005 | Pires | |
| 2007/0046482 A1 * | 3/2007 | Chan | A61F 13/42 340/604 |
| 2008/0243099 A1 | 10/2008 | Tippey et al. | |
| 2011/0263952 A1 | 10/2011 | Bergman et al. | |
| 2011/0295619 A1 | 12/2011 | Tough | |

FOREIGN PATENT DOCUMENTS

| | | |
|---|---|---|
| EP | 1433721 A1 | 6/2004 |
| EP | 2 158 887 | 3/2010 |
| EP | 2 241 298 | 10/2010 |
| IT | TO20120230 A1 | 6/2012 |
| JP | H08-508455 | 9/1996 |
| JP | 2008-272051 | 11/2000 |
| JP | 2009-519752 | 5/2009 |
| JP | 2010-537695 | 12/2010 |
| RU | 2286758 C2 | 11/2006 |
| WO | WO-96/14813 A1 | 5/1996 |
| WO | WO-00/00144 A2 | 1/2000 |
| WO | WO-2004/007316 A1 | 1/2004 |
| WO | WO-2004/100763 A2 | 11/2004 |
| WO | WO-2006/047815 A1 | 5/2006 |
| WO | WO 2007/070267 | 6/2007 |
| WO | WO 2009/027871 | 3/2009 |
| WO | WO-2011/054045 A1 | 5/2011 |
| WO | WO-2011/156862 A1 | 12/2011 |
| WO | WO-2013/136252 A2 | 9/2013 |

OTHER PUBLICATIONS

Extended European search report dated Oct. 19, 2016 issued in corresponding European patent application No. 13877891.5 (7 pages).

English-language translation of a Chinese Office Action dated Jul. 4, 2016 issued in corresponding Chinese patent application No. 201380074536.1 (11 pages).

First Russian Office Action dated Mar. 2, 2017 issued in corresponding Russian patent application No. 2015143440 (7 pages) and its English-language translation thereof (5 pages).

European Office Action dated Oct. 28, 2019 issued in European patent application No. 13 877 891.5 (4 pages).

* cited by examiner

DISPOSABLE ABSORBENT PRODUCTS IN A STACKED ARRANGEMENT

CROSS-REFERENCE TO PRIOR APPLICATION

This application is a § 371 National Stage Application of PCT International Application No. PCT/SE2013/050242 filed Mar. 14, 2013, which is incorporated herein in its entirety.

TECHNICAL FIELD

The present disclosure is generally related to absorbent products and, more particularly, to absorbent products available in stacked configurations.

BACKGROUND

Absorbent products, such as baby diapers, training pants, adult briefs, animal diapers, disposable swimming underwear, and incontinent pads, are typically designed to retain bodily waste such as feces, urine, blood, or menses secreted by the person or animal wearing the disposable absorbent product. It is often desirable to make those products available in a stacked configuration, such as to facilitate their transport and their availability in retail environments, such as store shelves.

In conventional stacked configurations, all the folded products face the same direction. For example, each product in a stack may be folded in half so as to have a front panel and a back panel, with all the front panels in the stack facing a common direction and all the back panels also facing a common direction, and further with all products being oriented with all folds lying in a common plane.

A problem with conventional stacked configurations of the type described above lies in that those configurations may result in a relatively tight side of the stack, corresponding to the location of the folds of the products (i.e., the common plane), and a relatively loose opposite side, corresponding to the terminal ends of the products. This difference may result in an uneven and possibly unstable stack of the products.

Further, some products have relatively loose components such as fasteners (e.g., landing zones) or waist features that are susceptible to separation from the rest of the product. Conventional stacked configurations often result in those features being in contact with components of an outer package containing the stack. Upon retrieval of some of those products from the stack, the relatively loose components may become entangled or otherwise come in contact with those components of the outer package, resulting in inadvertent separation of those components. Yet other products may have prints or other features on particular surfaces of the products that may be damaged by having abutting contact with the surfaces of the outer package.

It would be desirable, therefore, to provide stacked configurations for absorbent products that address these and other shortcomings of conventional stacks of those products.

SUMMARY

In one embodiment, a stack of disposable absorbent products is stacked along a stacking axis and includes a first plurality of folded disposable absorbent products. Each of the products is folded into at least two panels so as to define first and second ends and front and back oppositely-facing exterior faces of each of the first plurality of folded products, with the respective front faces of the first plurality of folded products facing a common, first direction. At least one folded disposable absorbent product is folded substantially in the same manner as the first plurality of folded products to thereby define first and second ends and front and back oppositely-facing exterior faces of the at least one folded product, with the front face of the at least one folded product facing a second direction opposite from the first direction. Each of the disposable absorbent products has a topsheet, a backsheet, and an absorbent core disposed between the topsheet and the backsheet for absorbing fluids secreted by a wearer of the disposable absorbent product.

The at least one folded product may be oriented about 180°, about the stacking axis, relative to an adjacent one of the first plurality of folded products. In a specific embodiment, the stack also has a second plurality of folded disposable absorbent products, with each of those products being folded substantially in the same manner as the first plurality of folded products to thereby define first and second ends and front and back oppositely-facing exterior faces of the second plurality of folded products. In that embodiment, the respective front faces of the second plurality of folded products face the first direction, and the first end of each of the second plurality of folded products is adjacent at least one of the second ends of the first plurality of folded products. Additionally, the first ends of the first plurality of folded products and the second ends of the second plurality of folded products may lie generally in a common plane.

In another specific embodiment, the at least one folded product and each of the first plurality of folded products include respective rigid components coupled to the front face or the back face of the respective folded product. The at least one folded product and each of the first plurality of folded products may additionally include a respective plurality of wires extending from the rigid component. Additionally or alternatively, the at least one folded product and each of the first plurality of folded products are respectively folded into 3 panels, with each respective rigid component being located adjacent or at a respective longitudinal end of the respective folded product in an unfolded condition. The at least one folded product is, in specific embodiments, located at one end of the stack.

In another embodiment, a package of disposable absorbent products is arranged in a stack, with the disposable absorbent products being stacked along a stacking axis. The package has a first plurality of folded disposable absorbent products, each folded into at least two panels so as to define front and back oppositely-facing exterior faces of each of the first plurality of folded products. The package also includes a second plurality of folded disposable absorbent products, each folded substantially in the same manner as the first plurality of folded products to thereby define front and back oppositely-facing exterior faces of the second plurality of folded products.

A first folded disposable absorbent product at an end of the stack is folded substantially in the same manner as the first and second pluralities of folded products to thereby define front and back oppositely-facing exterior faces of the first folded product at the end of the stack. The respective front faces of the first and second plurality of folded products face a common, first direction, and each of the second plurality of folded products is oriented about 180°, about the stacking axis, relative to the first plurality of folded products. The front face of the first folded product at the end of the stack faces a second direction opposite from the first direction.

In a specific embodiment, each of the first folded product at the end of the stack and the first and second pluralities of folded products includes respective rigid components coupled to the front face or to the back face of the folded product. Additionally, the first folded product at the end of the stack and each of the first and second pluralities of folded products may include respective pluralities of wires extending from the respective rigid component.

In another embodiment, a stack of absorbent products is provided. The stack includes a first plurality of absorbent products, each having a first end, a second end disposed opposite the first end, and first and second oppositely-facing exterior faces. The respective first faces of the first plurality of absorbent products face a common, first direction. The stack also includes at least one absorbent product having a first end, a second end disposed opposite the first end, and first and second oppositely-facing exterior faces of the at least one absorbent product. The first exterior face of the at least one absorbent product faces a second direction opposite from the first direction. In that embodiment, each of the absorbent products has an absorbent core for absorbing fluids secreted by a wearer of the absorbent product.

In a specific embodiment, the at least one absorbent product and each of the first plurality of absorbent products is a disposable absorbent product that includes a topsheet and a backsheet in confronting relationship with the topsheet. The absorbent core in that specific embodiment is disposed between the topsheet and the backsheet. The stack may additionally have a second plurality of absorbent products, each having a first end, a second end disposed opposite the first end, and first and second oppositely-facing exterior faces. The respective first exterior faces of that second plurality of absorbent products face the first direction. The first ends of the first plurality of absorbent products and the second ends of the second plurality of absorbent products may lie generally in a common plane.

In another specific embodiment, the at least one absorbent product and each of the first plurality of absorbent products include respective rigid components coupled to the first exterior face or the second exterior face of the absorbent product. Additionally or alternatively, the at least one absorbent product and each of the first plurality of absorbent products include respective pluralities of wires extending from the rigid component. The at least one absorbent product may be located at one end of the stack. The at least one absorbent product and each of the first plurality of absorbent products in a specific embodiment are respectively folded, so as to define at least two panels of each of the absorbent products.

In yet another embodiment, a stack of absorbent products is provided, with the absorbent products being stacked along a stacking axis. The stack has a plurality of absorbent products, each having first and second oppositely-facing exterior faces. The stack also has a first end absorbent product located at a first end of the stack, with the first end absorbent product having first and second oppositely-facing exterior faces, and a first rigid component coupled to the first exterior face or the second exterior face of that first end absorbent product. Additionally, the stack has a second end absorbent product located at a second end of the stack opposite the first end of the stack. The second end absorbent product has first and second oppositely-facing exterior faces and a second rigid component coupled to the first exterior face or the second exterior face of that absorbent product.

Each of the plurality of absorbent products, the first end absorbent product, and the second end absorbent product, have respective absorbent cores for absorbing fluids secreted by a wearer of the respective absorbent product. Further, the first and second end absorbent products are respectively oriented in the stack such that the first and second rigid components face toward a center of the stack. The first and second end absorbent products may have respective pluralities of wires extending from the first and second rigid components. Additionally or alternatively, each of the plurality of absorbent products has a respective rigid component coupled to the respective first or second exterior face of that absorbent product. In a specific embodiment, the at least one absorbent product and each of the first plurality of absorbent products are respectively folded so as to define at least two panels of the absorbent product.

BRIEF DESCRIPTION OF THE DRAWINGS

Embodiments of the invention are described in the following detailed description taken in conjunction with the accompanying drawings in which.

DETAILED DESCRIPTION OF PARTICULAR EMBODIMENTS

To the extent that any meaning or definition of a term in this written document conflicts with any meaning or definition of that term in a document incorporated by reference, the meaning or definition assigned to that term in this written document shall govern. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Further, "connected" and "coupled" are not restricted to physical or mechanical connections or couplings.

Figure 1:
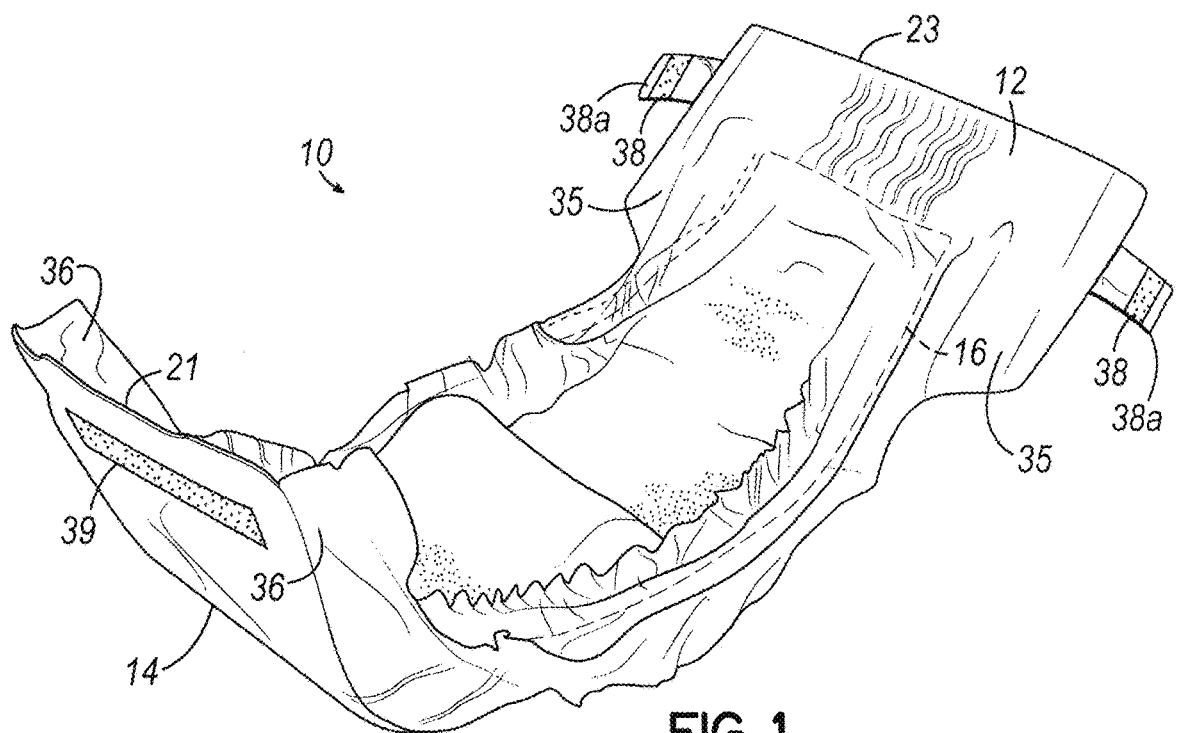
FIG. 1 is a perspective view of a absorbent product in accordance with one embodiment of the invention.
Figure 1A:
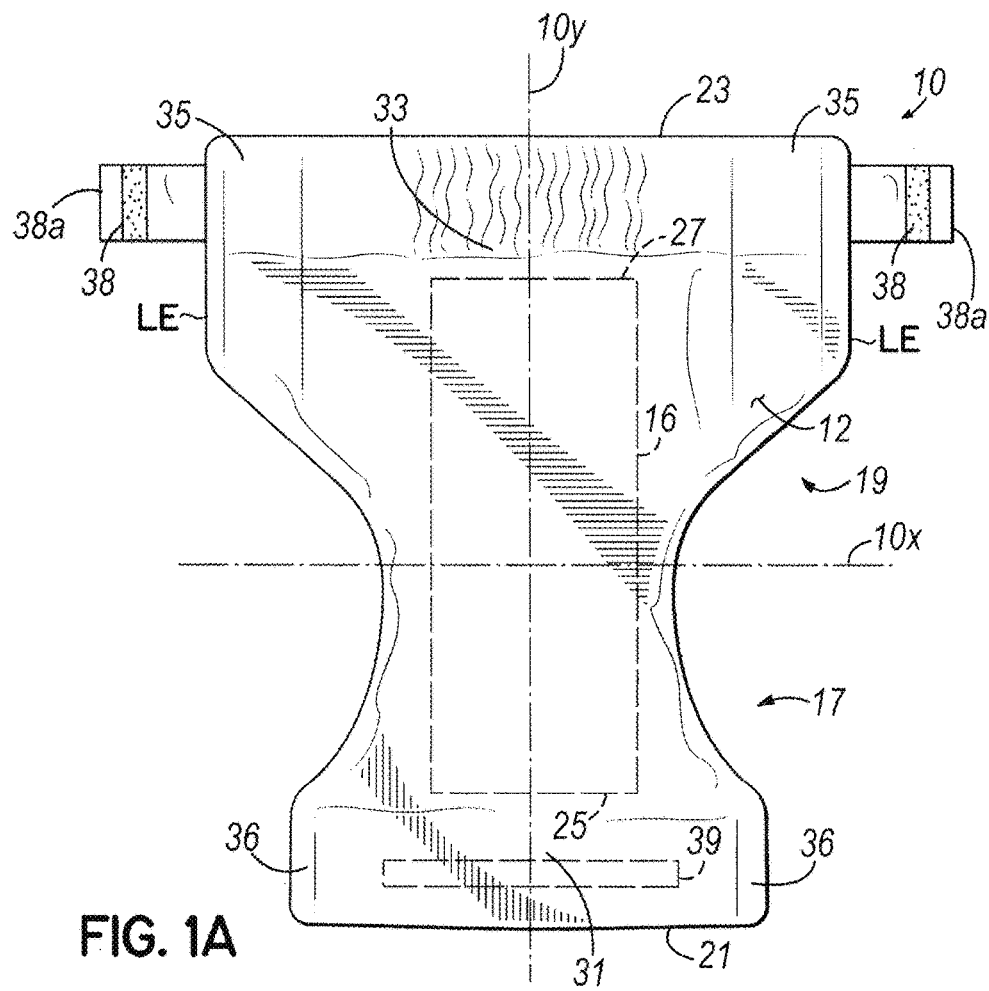
FIG. 1A is a top view of the product of FIG. 1.

With reference to the figures, and more particularly to FIGS. 1 and 1A, an exemplary disposable absorbent product, such as an open diaper 10 is illustrated in an unfolded condition. While the description herein refers to features of the diaper 10, or features of a stack of the diapers 10, it is understood that the description is also applicable to other types of disposable absorbent products intended to contain human or even animal secreted fluids and solids, such as feces, urine, blood, or menses. In that regard, the present description is similarly applicable to closed (i.e., pant-like) diapers, open and closed adult briefs, sanitary napkins, disposable swimwear, light or heavy incontinence pads, training pants, and other similar products. Likewise, while the present description refers to a disposable-type diaper 10, the features of the various embodiments described herein are similarly applicable to non-disposable absorbent products, which are intended to be at least partially washed and re-used.

Diaper 10 extends in the longitudinal direction along a longitudinal axis $10y$, and extends laterally along a transverse axis $10x$ orthogonal to the longitudinal axis $10y$. Diaper 10 has a topsheet 12 and a backsheet 14 disposed opposite the topsheet 12, such that the topsheet 12 and backsheet 14 are in an overlaying relationship with one another. An absorbent core 16 is disposed between the topsheet 12 and backsheet 14, as more fully explained below.

The topsheet 12 is at least partially made of a permeable, hydrophilic material such as a hydrophilic nonwoven, and may be in the form of a single, continuous layer spanning across the length and/or width of the diaper 10, or may alternatively be in the form of two or more layers of the same material or of materials different from one another that jointly, rather than individually, span the length and/or width of the diaper 10. In that regard, the term "topsheet" as used herein can refer to a single layer that lies over the absorbent core 16 as well as partially or entirely over regions laterally outboard of the core 16, or can alternatively refer to a plurality of layers of material joined to one another so as to span the entire width of diaper 10.

The backsheet 14 is at least partially made of an impermeable, hydrophobic material, such as a hydrophobic nonwoven or a laminate made of one or more layers of nonwoven material and one or more layers of polypropylene or polyethylene film. Backsheet 14 may be in the form of a single, continuous layer spanning across the length and/or width of the diaper 10, or may alternatively be in the form of two or more layers of the same material or of materials different from one another that jointly, rather than individually, span the length and/or width of the diaper 10.

The diaper 10 also includes, as discussed above, an absorbent core 16, disposed between the topsheet 12 and the backsheet 14. The core 16 is configured to absorb and retain bodily fluids, such as watery feces, urine, blood, and/or menses, secreted by the wearer. The core 16 may be made up of fluff pulp or a combination of fluff pulp or some other natural or synthetic fluid management material, and a fluid storage material such as superabsorbent material ("SAP") or some other natural or synthetic fluid storage material. While not shown, core 16 may also include an optional acquisition material layer or another type of layer (e.g., an airlaid material layer) adjacent the topsheet 12, which is primarily configured to distribute and/or direct fluids received through the topsheet 12 onto other portions of core 16 that are primarily configured to store fluids secreted by the wearer.

The core 16 could be generally rectangular, or have an hourglass shape, or have any other regular or irregular, symmetrical or asymmetrical shape.

With continued reference to FIGS. 1 and 1A, the transverse axis $10x$ conceptually divides the diaper 10 into front and back longitudinal hemispheres 17, 19. The diaper 10 thus extends longitudinally between a front longitudinal end 21 and a back longitudinal end 23. The core 16, in turn, extends longitudinally between a front edge 25 and a back edge 27. While the front and back edges 25, 27 are illustrated in the figures as generally rectilinear, it is understood that either or both may have any other regular or irregular shape, such as one including curves, straight line segments or any other shape. The front longitudinal end 21 and the front edge 25 fall generally within the front portion of the diaper 10 which, in use, generally faces the front part of the body of the wearer. In contrast, the back longitudinal end 23 and the back edge 27 fall generally within the back portion of the diaper 10, which generally faces the back part of the body of the wearer. In this regard, and as used herein, the terms "front portion" and "back portion," when used to describe parts of the diaper 10, do not imply the existence of any specific structural boundaries within the diaper 10, but instead refer to the general areas that, in use, lie respectively against the front and back regions of the body of the wearer. The diaper 10 is also considered to include a crotch portion located between the front and back portions thereof, which is a region of diaper 10 that generally lies against the crotch of the wearer, in use.

The core 16 of the illustrated embodiment is positioned, relative to other portions of the diaper 10, such that a front end portion 31 is defined between the front longitudinal end 21 and the front edge 25 of the core 16. The exemplary core 16 is also positioned so as to define a back end portion 33 between the back longitudinal end 23 and the back edge 27 of the core 16. Those of ordinary skill in the art will readily appreciate, however, that other relative positions of the core 16 are possible which may, for example, define only one end portion 31, 33 or define no such end portions at all. In other words, alternative configurations are contemplated in which the core 16 may instead extend to one or both of the longitudinal ends 21, 23.

With continued reference to FIGS. 1 and 1A, diaper 10 includes a pair of side regions in the form, in this embodiment, of side panels 35, laterally outboard of the core 16 in the back portion of the diaper 10. The side panels 35 are thus made up of portions of the topsheet 12 and backsheet 14 that are joined together with adhesive elements, thermally (e.g., heat-bonding) and/or mechanically (e.g., CPW or ultrasonic bonding), for example, so as to form an integral structure. In specific embodiments, the side panels 35 may include elastomeric portions (not shown) that allow the side panels 35 to laterally stretch with relative ease, to accommodate convenient application of diaper 10 and provide comfort to the wearer. The elastomeric portions may in some embodiments extend into areas directly beneath the core 16. The exemplary diaper 10 similarly has another pair of side regions 36, also laterally outboard of core 16, but located generally in the front portion of the diaper 10. The construction of the side regions 36 is generally similar to that of the side panels 35, which may for example optionally include elastomeric portions (not shown) similar to or different from the optional elastomeric portions in side panels 35.

Diaper 10 has a pair of fastening components such as mechanical fasteners or adhesive or cohesive tapes, generally assigned the numeral 38, located in the back portion of diaper 10. In the illustrated embodiment, the fastening components 38 are supported on respective tabs 38a that extend outwardly from the lateral ends LE in the back portion of diaper 10. Other embodiments are also contemplated within the scope of the present disclosure, in which the fastening components 38 are supported directly on the side panels 35, rather than on tabs, and located generally adjacent the lateral ends LE in the back portion of diaper 10.

The fastening components 38 are engageable with a cooperating fastening component or feature 39 in the front portion of the diaper 10 to secure the diaper 10 in place, on the body of the wearer. The cooperating fastening feature 39 may for example be in the form of an adhesive or cohesive landing zone or patch, or a mechanical fastener landing zone or patch (e.g., containing hooks or loops) coupled (e.g., mechanically and/or adhesively attached) to the backsheet 14 and which cooperates with fastening components 38 to secure the diaper 10 in place, on the body of the wearer. In the exemplary embodiment of FIGS. 1 and 1A, the fastening components 38 include hook members and the cooperating fastening feature 39 includes a loop member. Entangled engagement of the hook and loop members with one another secures the front and back portions of diaper 10 to one another on the body of the wearer. Other embodiments are similarly contemplated in which the fastening components 38 are loop members that are engageable with a hook-type fastening feature 39. Yet other embodiments are contemplated in which fastening feature 39 includes two or more hook fasteners or loop fasteners, rather than a single structure (e.g., as in the exemplary single structure making up fastening feature 39 in FIGS. 1 and 1A).

Fastening feature 39 may alternatively be defined by the exterior surface of the backsheet 14, so long as that surface is configured to directly entangle the fastening component 38 sufficiently so as to secure the diaper 10 in place i.e., on the body of the wearer. While the embodiment of FIGS. 1 and 1A has the fastening components 38 located in the back portion of diaper 10 and the cooperating fastening feature 39 located in the front portion, embodiments are contemplated in which the fastening components 38 are instead located in the front portion of diaper 10, while the cooperating fastening feature 39 is located in the back portion of diaper 10, so long as they are positioned so as to engage one another to secure the diaper 10 in place on the body of the wearer.

Figure 2:
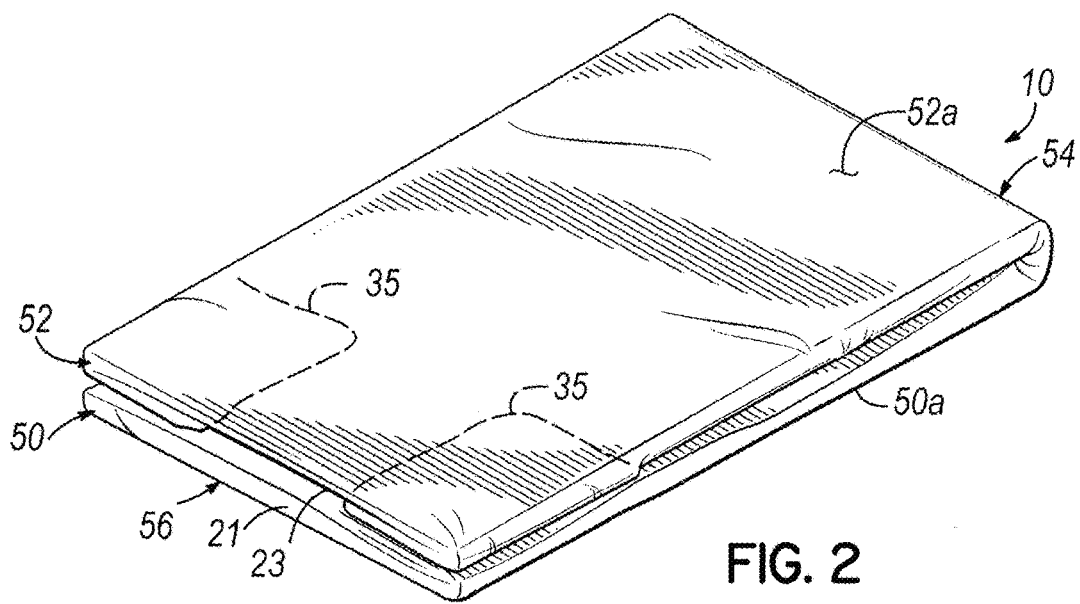
FIG. 2 is a perspective view of the product of FIGS. 1 and 1A in an exemplary folded configuration.
Figure 3:
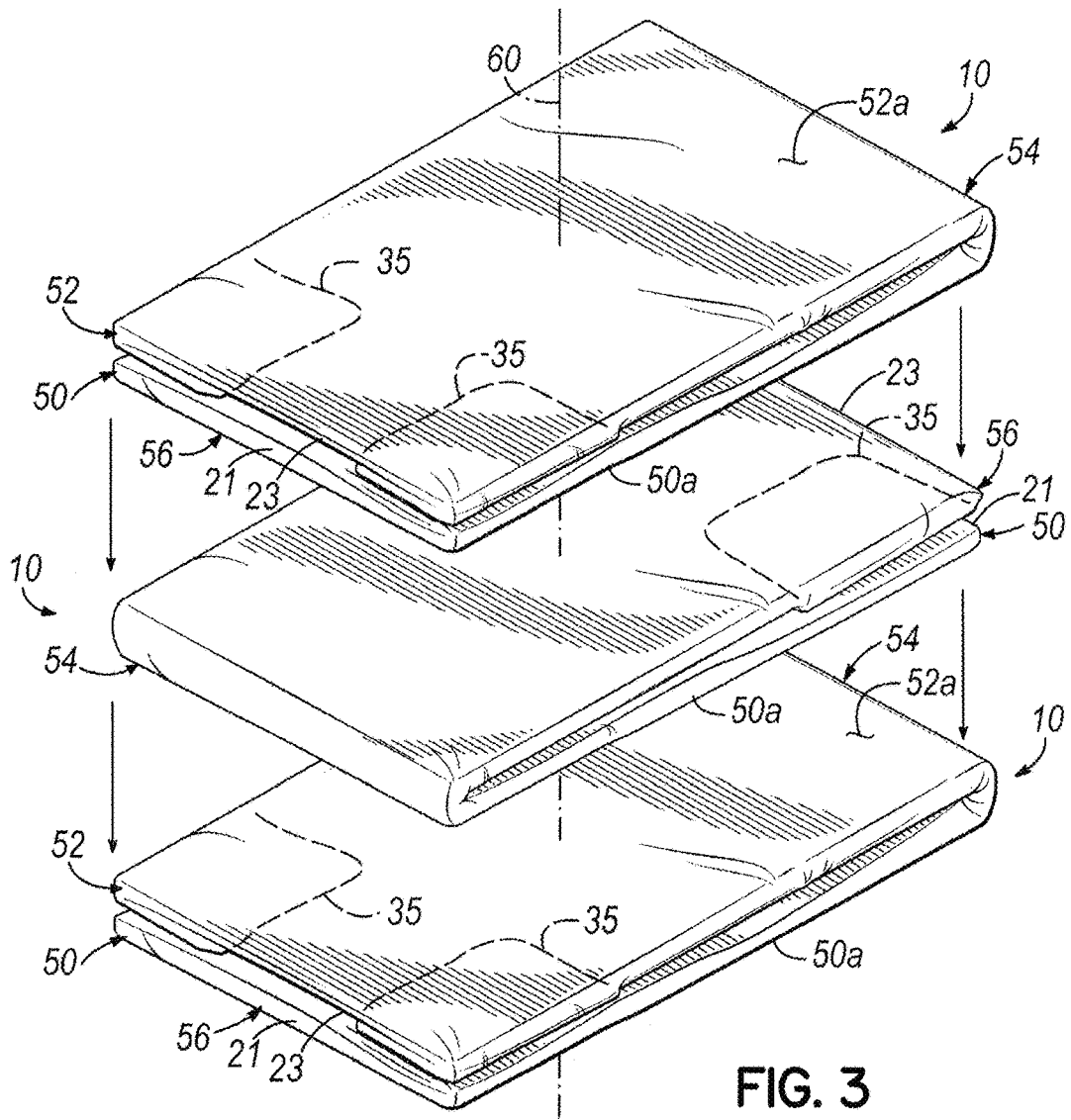
FIG. 3 is a perspective view of an exemplary formation of a stack of products of the type shown in FIGS. 1, 1A, and 2.
Figure 4:
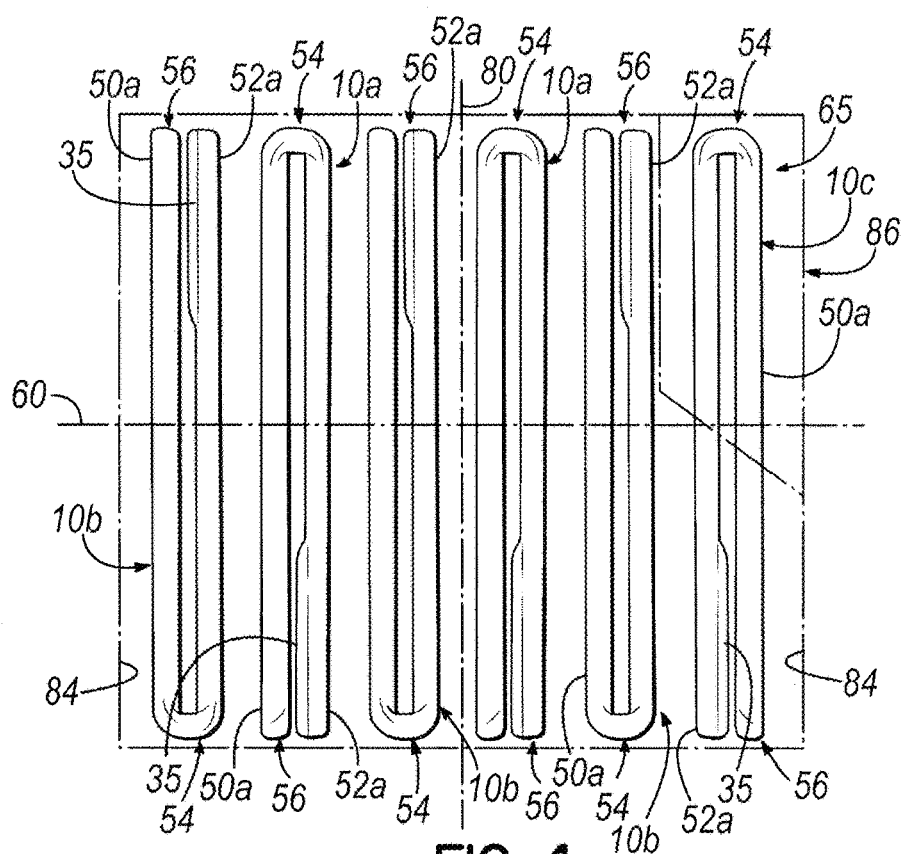
FIG. 4 is a schematic elevation view of a plurality of products of the type shown in FIGS. 1, 1A, 2, and 3 in an exemplary stacked configuration.

With continued reference to FIGS. 1 and 1A, and further referring to FIGS. 2, 3, and 4, diaper 10 may be folded in a number of configurations to facilitate packaging of a stack of diapers 10. FIG. 2, in particular, illustrates an exemplary bifolded diaper 10, with the folding defining a pair of panels 50, 52 of the folded diaper 10 with respective oppositely-disposed exterior faces 50a, 52a. For ease of explanation, panel 50 is referredto herein as the "front panel" of folded diaper 10, generally coinciding with the front portion of diaper 10. Similarly, and also for ease of explanation, panel 52 is referredto herein as the "back panel" of folded diaper 10, generally coinciding with the back portion of diaper 10. The exterior faces 50a, 52a are, for the same reasons, and in non-limiting fashion, respectively referredto herein as "front face 50a" and "back face 52a."

In the exemplary embodiment of FIG. 2, the folding of diaper 10 is further such that the side panels 35 and side regions 36 are tucked inwardly, and are therefore substantially unexposed to the exterior of folded diaper 10. Alternatively, it is contemplated that the side panels 35 and/or the side regions 36 may be exposed to the exterior of folded diaper 10 in alternative folding configurations (not shown). In the embodiment of FIG. 2, the exemplary folding of diaper 10 also defines a first end 54 and a second end 56 of the folded diaper 10. As used herein, the terms "first" and "second" when referring to ends 54, 56 of folded diaper 10 are not intended to be tied to any specific structural components or portions of the diaper 10.

For ease of explanation, however, the "first" end of folded diaper 10 is used herein to refer to the end coincident with the fold of diaper 10, while the "second" end denotes the opposite end coincident, in the exemplary folding of FIGS. 2-4, with the front and back longitudinal ends 21, 23 of diaper 10 i.e., in the unfolded condition (FIGS. 1 and 1A). While the exemplary folding configuration of FIGS. 2-4 results in the panels 50, 52 having generally the same length and width, it is contemplated that they may alternatively have dimensions that are different from one another, and still fall within the scope of the present disclosure.

FIGS. 3 and 4 illustrate an exemplary stacked configuration of folded diapers 10. The folded diapers 10 are stacked along a stacking axis 60 to thereby form a stack 65. The stack 65 has first and second pluralities of folded diapers 10a, 10b, oriented upside down relative to one another. More specifically, each of the folded diapers 10b is oriented about 180°, about the stacking axis 60, relative to the folded diapers 10a. Further, in the exemplary stacked configuration of FIGS. 3 and 4, the folded diapers 10a and 10b are arranged in alternating fashion so that each folded diaper 10a is adjacent at least one, if not two, of the folded diapers 10b. While the folded diapers 10a, 10b are illustrated in FIG. 4 as being spaced from one another, it is understood that such representation is schematic, and therefore not intended to be limiting. More specifically, the folded diapers 10a, 10b in that figure may be in a compressed state, thereby leaving substantially no spaces between adjacent ones of the folded diapers 10a, 10b. In the embodiment of FIGS. 3 and 4, each respective first end 54 of a folded diaper 10a, 10b is adjacent at least one second end 56 of an adjacent folded diaper 10a, 10b. This type of arrangement facilitates formation of a uniform stack of folded diapers 10a, 10b, by evenly distributing the relatively thicker fold region (coincident with the first end 54) of the folded diapers 10a, 10b. The exemplary folding and stacking illustrated at FIGS. 2-4 also result in the first and second ends 54, 56 of adjacent folded diapers 10a, 10b lying generally in a common plane, and also result in the folded diapers 10a, and the folded diapers 10b, all having their respective front faces 50a facing a common direction (to the left, in the orientation of FIG. 4) and their respective back faces 52a also facing a common direction (to the right, in the orientation of FIG. 4).

The exemplary stack 65 of FIG. 4 also has a folded diaper 10c at one end of the stack 65, which is upside down (i.e., oriented about 180° about stacking axis 60) relative to the folded diaper 10b adjacent thereto. Folded diaper 10c is further oriented about 180° about an axis 80, orthogonal to the stacking axis 60, relative to the adjacent diaper 10b. In that regard, the orientation of the end folded diaper 10c is such that the front face 50a of that folded diaper 10c faces a direction opposite the facing direction of front face 50a of the adjacent diaper 10b. In the illustrative embodiment of FIG. 4, and relative to the orientation shown therein, the front face 50a of folded diaper 10c faces right, while the front face 50a of the adjacent folded diaper 10b faces left. More specifically, the back face 52a of folded diaper 10c faces the back face 52a of the adjacent folded diaper 10b, and their respective front faces 50a face away from one another.

With continued reference to FIGS. 3 and 4, it is contemplated that folded diapers 10a and 10b may be arranged in ways that are different from the arrangement shown in those figures. For example, an alternative stack may have the folded diapers 10a and the folded diapers 10b in alternating groups of two or more folded diapers each. More specifically, an alternative stack may have for example a group of three folded diapers 10a adjacent a group of three folded diapers 10b, which is followed by an adjacent group of three folded diapers 10a, and so on. Other alternative stacks may have a group of folded diapers 10a (e.g., 3 diapers) in a predetermined number, followed by an adjacent group of folded diapers 10b in a different number. Yet other alternative stacks have all the folded diapers in the orientation of diapers 10a or the orientation of diapers 10b, and/or one or more folded diapers in the orientation of exemplary folded diaper 10c, located at an end of the stack or somewhere other than at an end of the stack. Another alternative stacked configuration is contemplated, similar in most respects to the embodiment illustrated in FIG. 4, but in which the end folded diaper 10e is not upside down relative to the adjacent folded diaper 10b, but which instead is oriented such that the first end 54 of that end folded diaper 10c is adjacent the first end 54 of the adjacent folded diaper 10b, rather than being adjacent the second end 56 of adjacent folded diaper 10b, as in the embodiment of FIG. 4.

While not shown, a contemplated alternative embodiment of a stack of folded diapers has one or more pairs of adjacent folded diapers oriented such that the respective front faces 50a or the respective back faces 52a thereof face one another. This may be advantageous, for example, in cases in which it is intended for a consumer to pull the folded diapers from the stack in pairs, rather than individually.

In the embodiment of FIG. 4, the back face 52a of one of the folded diapers (i.e., folded diaper 10c) at an end of the stack 65 is oriented so as to avoid contact between the back face 52a and the adjacent end wall 84 of an outer packaging enclosure 86 (e.g., cardboard box, film wrap) enveloping the stack 65. This may be advantageous when the back face 52a of each of the folded diapers 10a, 10b, 10c has a loosely attached component (e.g., a landing zone fastener) that may become entangled with the surface or other feature of the end wall 84, particularly when the stack 65 is stacked under pressure, thereby exerting an outward, expansive force against each of the two opposing end walls 84 of packaging enclosure 86. For example, upon retrieval of the end folded diaper 10c through an opening 88 of outer packaging enclosure 86, the frictional engagement of back face 52a with the adjacent end wall 84 may otherwise cause the loosely attached feature to separate from the rest of the folded diaper 10c. Thus, the particular orientation of the folded diaper 10c in the embodiment of FIG. 4 prevents that from happening.

The relative orientation of the back face 52a of folded diaper 10c at an end of the stack 65 may be also advantageous in situations in which the back face 52a has a print or some other feature that may be damaged through mere contact with the abutting adjacent end wall 84. For example, the back face 52a of folded diaper 10c may have a print made of an ink that may react when placed in contact with a chemical present on the interior surface of the adjacent end wall 84. Avoiding such contact, accordingly, would prevent damage to that print.

Figure 5:
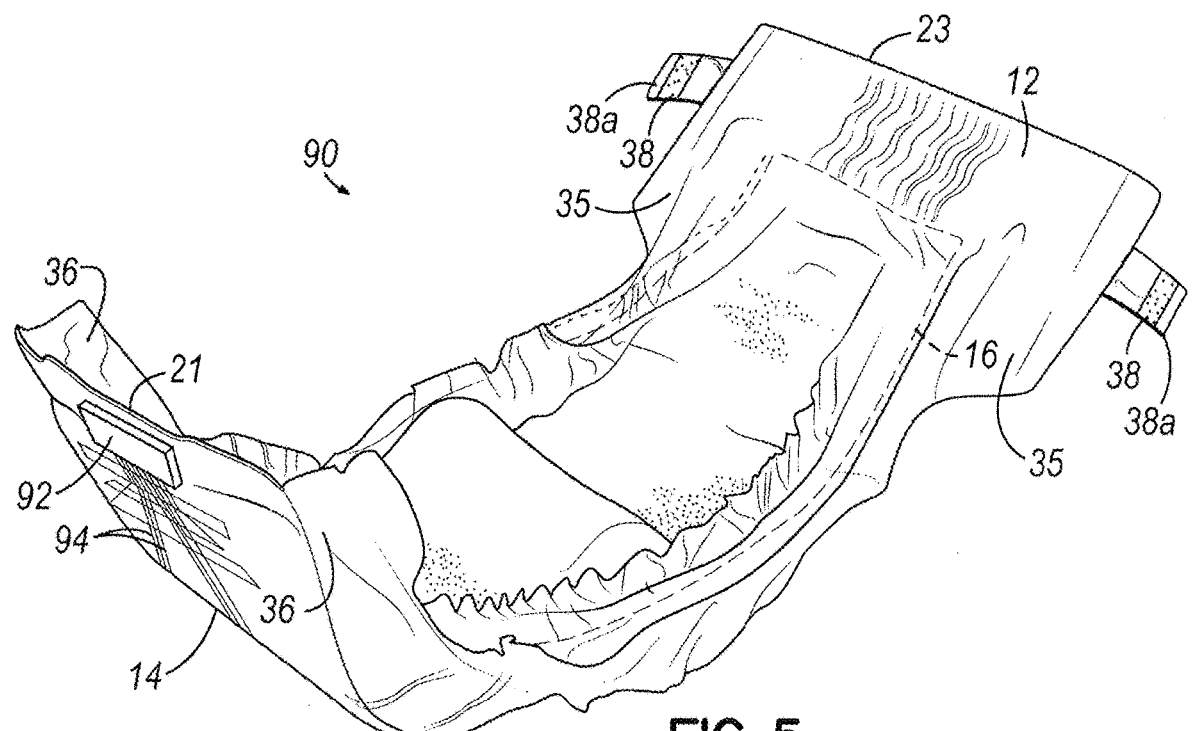
FIG. 5 is a perspective view of an absorbent product in accordance with another embodiment of the invention.
Figure 6:
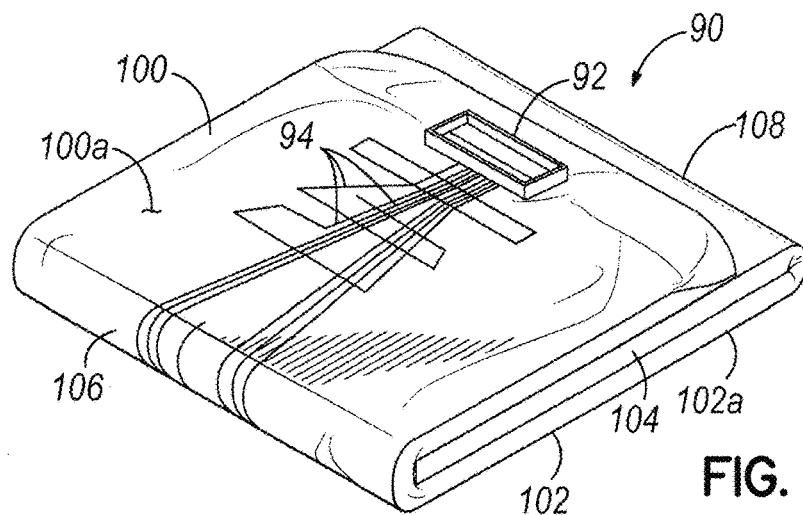
FIG. 6 is a perspective view of the product of FIG. 5 in an exemplary folded configuration.

With reference to FIGS. 5 and 6, an exemplary embodiment of an adult brief 90 is illustrated. For ease of understanding, like reference numerals in FIGS. 5 and 6 refer to similar features in the preceding figures, the description and illustration of which may be referredto for an understanding of the features of the embodiment in FIGS. 5 and 6 as well. Brief 90 has a rigid component 92, as well as a plurality of wires 94 extending from the rigid component 92. The rigid component 92, in a specific embodiment, may be an electronic interface device, made out of a hard plastic, metal, and/or other rigid material, connected to sensors (not shown) in brief 90, through the wires 94. As used herein, the term "rigid material" refers to a hard plastic or some other material that tends to break in response to sufficient deformation and, thus, has small plastic and/or elastic deformation range. In the exemplary brief 90 of FIGS. 5 and 6, the rigid component 92 is located adjacent the front longitudinal end 21 of brief 90 i.e., when in the unfolded condition of brief 90 (as in FIG. 5). It is contemplated, however, that the rigid component 92 may be instead located adjacent the back longitudinal end 23 of brief 90 (in its unfolded condition), or even located at either of those longitudinal ends 21, 23 so as to partially define the longitudinal ends 21, 23, or located elsewhere on brief 90.

Referring particularly to FIG. 6, that figure illustrates an exemplary folding configuration of the brief 90. The brief 90 in that figure is "C-folded" into three panels. More specifically, the brief 90 is folded so as to define a pair of outer panels 100, 102, and a central panel 104 disposed between the outer panels 100, 102. For ease of understanding, and without limitation, the outer panel 100 is herein denoted the "front panel 100," and the outer panel 102 is herein denoted the "back panel 102," with such denominations not intended to be tied to any particular structural elements of the brief 90. The front and back panels 100, 102 define respective oppositely-disposed exterior faces 100a, 102a of the folded brief 90. The exemplary rigid component 92 is coupled to and protrudes from the front face 100a of each of the folded briefs 90. Alternatively, coupling of the rigid component 92 to the front face 100a may be such that the rigid component 92 is located underneath, i.e., it is covered by, the material defining the front face 100a e.g., the backsheet 14 (FIG. 5) of the folded brief 90.

In the exemplary embodiment of FIG. 6, the folding of brief 90 is further such that the side panels 35 and side regions 36 (FIG. 5) are tucked inwardly, and are therefore substantially unexposed to the exterior of folded brief 90. Alternatively, it is contemplated that the side panels 35 and/or the side regions 36 may be exposed to the exterior of folded brief 90 in alternative folding configurations (not shown). In the embodiment of FIG. 6, the exemplary folding of brief 90 also defines a first end 106 and a second end 108 of the folded brief 90. As used herein, the terms "first" and "second" when referring to ends 106, 108 of folded brief 90 are not intended to be tied to any specific structural components or portions of the brief 90. For ease of explanation, however, the "first" end of folded brief 90 refers to the end coincident with the thicker of the two transverse folds of brief 90, which defines the outer panels 100 and 102, while the "second" end refers to the opposite end coincident, in the exemplary folding of FIG. 6, with the fold defining outer panel 102 and central panel 104. Those of ordinary skill in the art will readily appreciate that while the exemplary folding configuration of FIG. 6 illustrates the panels 100, 102, 104 having generally the same length and width, any two or even all three of the panels 100, 102, 104 may alternatively have dimensions that are different from one another, and still fall within the scope of the present disclosure.

Figure 7:
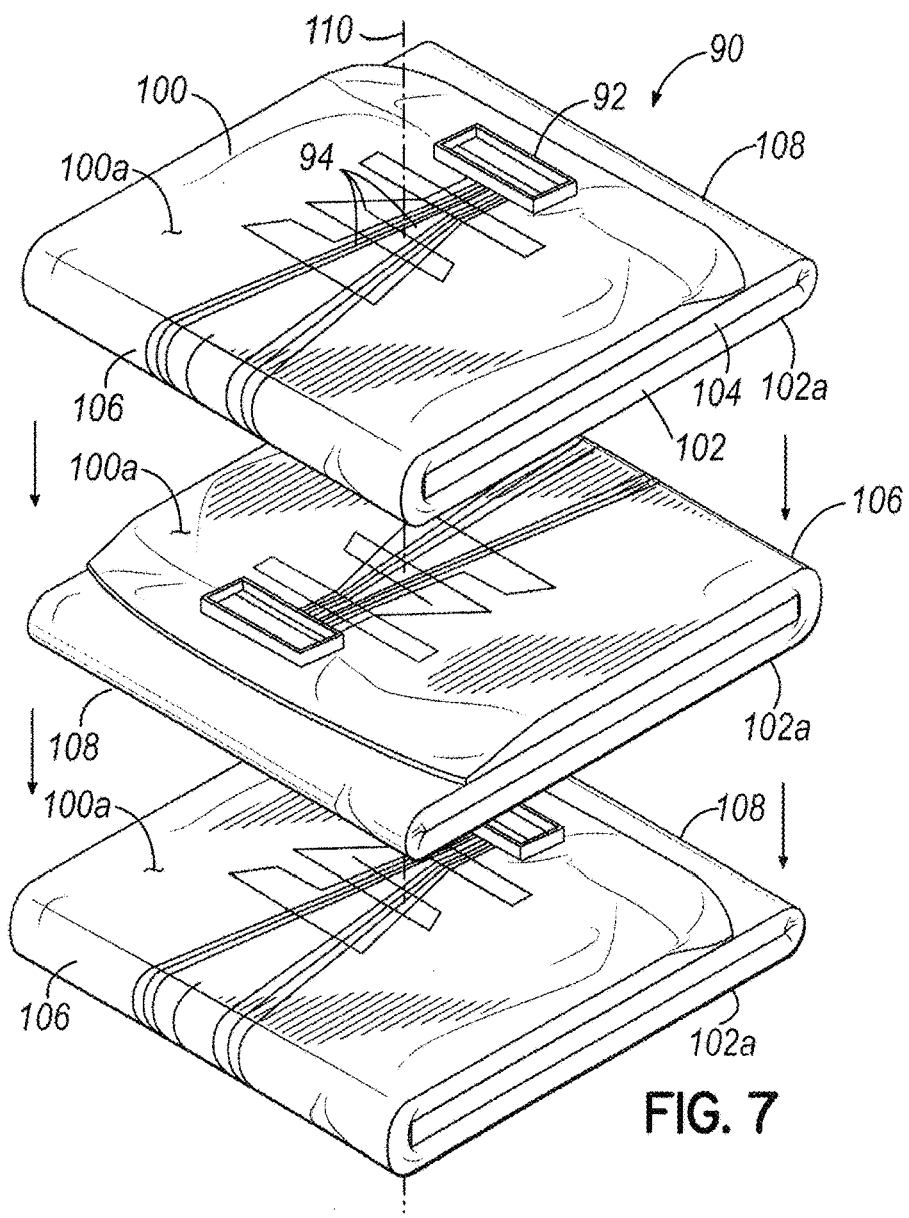
FIG. 7 is a perspective view of an exemplary formation of a stack of products of the type shown in FIGS. 5 and 6.
Figure 8:
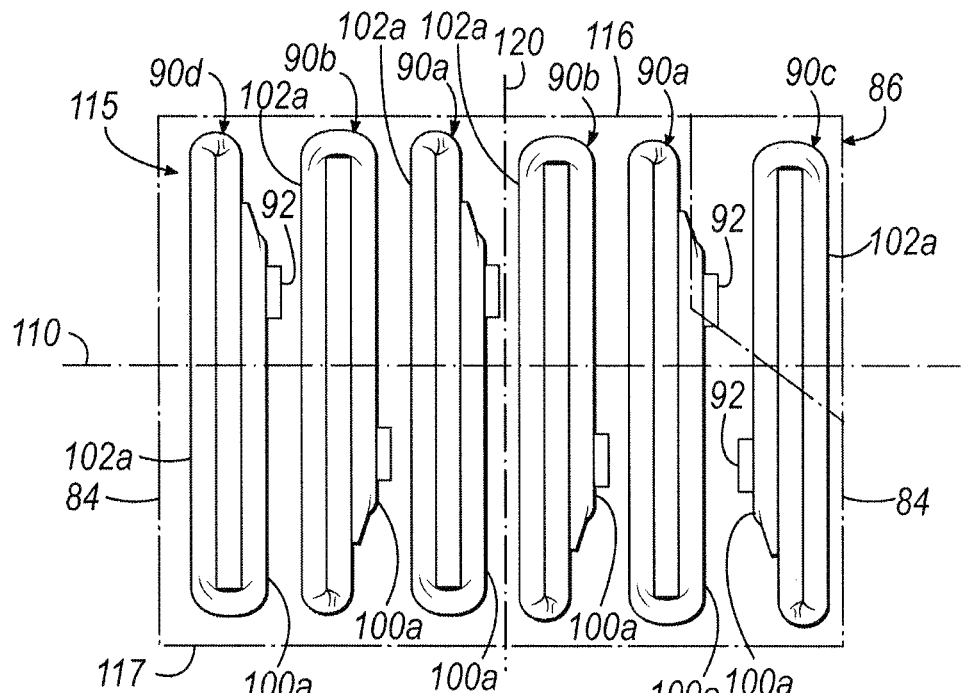
FIG. 8 is a schematic elevation view of a plurality of products of the type shown in FIGS. 5-7 in an exemplary stacked configuration.

FIGS. 7 and 8 illustrate an exemplary stacked configuration of the folded briefs 90. In those figures, the folded briefs 90 are stacked along a stacking axis 110 to thereby form a stack 115 of the folded briefs 90. The exemplary stack 115 has first and second pluralities of folded briefs 90a, 90b, oriented upside down relative to one another. More specifically, each of the folded briefs 90b is oriented about 180°, about the stacking axis 110, relative to the folded briefs 90a. Further, in the exemplary stacked configuration of FIGS. 7 and 8, the folded briefs 90a and 90b are arranged in alternating fashion so that each folded brief 90a is adjacent at least one, if not two, of the folded briefs 90b. This embodiment facilitates formation of a uniform stack of folded briefs 90a, 90b, by evenly distributing the relatively thicker fold region (coincident with the first end 106) of the folded briefs 90a, 90b. The exemplary folding and stacking illustrated at FIGS. 7 and 8 also result in the first and second ends 106, 108 of adjacent pairs of folded briefs 90a, 90b lying generally in a common plane, and in the folded briefs 90a, and the folded briefs 90b, all having their respective front faces 100a facing a common direction (to the right, in the orientation of FIG. 8). In addition, the respective back faces 102a of briefs 90a, 90b also face a common direction (to the left, in the orientation of FIG. 8).

Referring particularly to FIG. 8, the exemplary stack 115 illustrated in that figure also has a folded brief 90c at one end of the stack 115 that is upside down (i.e., oriented about 180° about stacking axis 110) relative to the adjacent brief 90a. Further, the folded brief 90c is oriented about 180° about an axis 120, orthogonal to the stacking axis 110, relative to the adjacent brief 90a. In that regard, the orientation of the folded brief 90c is such that the front face 100a of folded brief 90c faces a direction opposite the facing direction of front face 100a of the adjacent brief 90a. In the illustrative embodiment of FIG. 8, and relative to the orientation shown in that figure, the front face 100a of folded brief 90c faces left, while the front face 100a of the adjacent folded brief 90a faces right i.e., their respective front faces 100a face one another.

While not shown, alternative embodiments are contemplated in which the stack includes one or more folded briefs oriented similarly to folded brief 90c, located at an end of the stack, or elsewhere along the stack. Yet other alternative embodiments are contemplated having one or more pairs of adjacent folded briefs in which the respective front faces 100a or the respective back faces 102a of the adjacent folded briefs in the pair face one another. This may be advantageous, for example, in situations in which it is desirable for the surfaces of adjacent folded briefs that include rigid components 92 to face one another.

In the embodiment of FIG. 8 the front face 100a of a folded brief 90c at the end of the stack 115 is oriented so as to avoid contact between the front face 100a and the adjacent end wall 84 of the outer packaging enclosure 86 enveloping the stack 115. This may be advantageous when it is desired to avoid potential entanglement between the rigid component 92 of folded brief 90c with the surface or other feature of the adjacent end wall 84, particularly when the stack 115 is under pressure, thereby exerting an outward, expansive force against each of the end walls 84. In that regard, it is understood that while FIG. 8 is schematically drawn to depict the folded briefs 90a, 90b, 90c as being spaced from one another, stacking under pressure may result in adjacent folded briefs that have substantially no spacing between them.

Figure 8A:
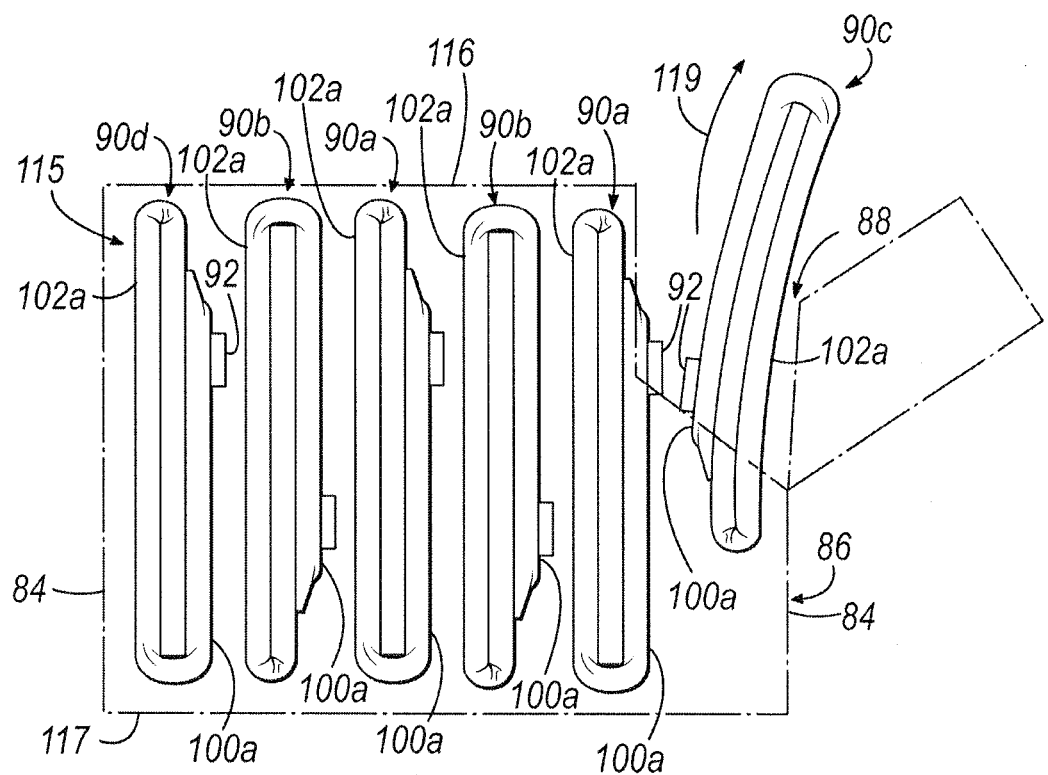
FIG. 8A is a view similar to FIG. 8, schematically illustrating one of the products being retrieved from the stack.

With particular reference to FIG. 8A, that figure illustrates exemplary retrieval of the end folded brief 90c through the opening 88 of outer packaging enclosure 86. As that figure shows, the exemplary orientation of folded brief 90c results in that folded brief being pulled upwards (arrow 119) through opening 88, while avoiding any potential entangling engagement of rigid component 92 with the adjacent end wall 84. This avoidance of contact between rigid component 92 and adjacent end wall 84 prevents or at least minimizes potential separation of rigid component 92 from the rest of the folded brief 90c, which may otherwise occur if rigid component 92 was in contact with adjacent end wall 84 during retrieval of folded brief 90c. Further, the avoidance of contact may be also desirable to prevent damage to the enclosure 86 due to frictional or other type of engagement between rigid component 92 and adjacent end wall 84. For example, the enclosure 86 may be made of a relatively thin film that is susceptible to damage by virtue of stress induced by engagement with rigid component 92.

In the embodiment of FIGS. 8 and 8A, a folded brief 90d at the opposite end of the stack 115 i.e., opposite from folded brief 90c, is also oriented such that its respective rigid component 92 faces away from the end wall 84 adjacent that folded brief. Accordingly, in that embodiment, both of the respective components 92 of the folded briefs 90c, 90d at the respective ends of the stack 115 face inwardly, toward the center of the stack 115, which minimizes the likelihood of contact between those rigid components 92 and the enclosure 86. Additionally, in the exemplary embodiment of FIGS. 8 and 8A, the folding of each of the briefs 90a, 90b, 90c, 90d in the stack 115 is such that all rigid components 92 are located at a suitably chosen distance from the top and bottom walls 116, 117 of enclosure 86. This further minimizes the likelihood of contact between the rigid components 92 and any portion of enclosure 86. In a specific embodiment, the rigid components are located at a distance of at least about 20 mm from either of the top and bottom walls 116, 117, although other distances are similarly contemplated.

The exemplary orientation of the front face 100a of the folded brief 90c at an end of the stack 115 is also advantageous in other situations. For example, this orientation may be desirable in situations in which the materials or structural elements of rigid component 92 or the front face 100a would be damaged by having contact with the material or structural elements of adjacent end wall 84, with which the folded brief 90c abuts, due to a chemical reaction between abutting materials.

While not shown, it is contemplated that folded briefs 90a, 90b, 90c may instead, or in addition, have a rigid component 92 or some other component coupled to the back face 102a of the respective folded brief, and which is susceptible to damage if placed in prolonged contact with the adjacent end wall 84 or with another wall, or even with some component of an adjacent folded brief. The stacked arrangement of the folded briefs 90 may in that case include orienting each of the folded briefs 90 so that their respective back faces 102a face in a direction different from the facing direction of the back face 102a of an adjacent folded brief. This facilitates preventing or at least minimizes contact of the back faces 102a with specific surfaces or components of adjacent packaging materials or structures, or materials or structures forming part of adjacent folded briefs.

Figure 8B:
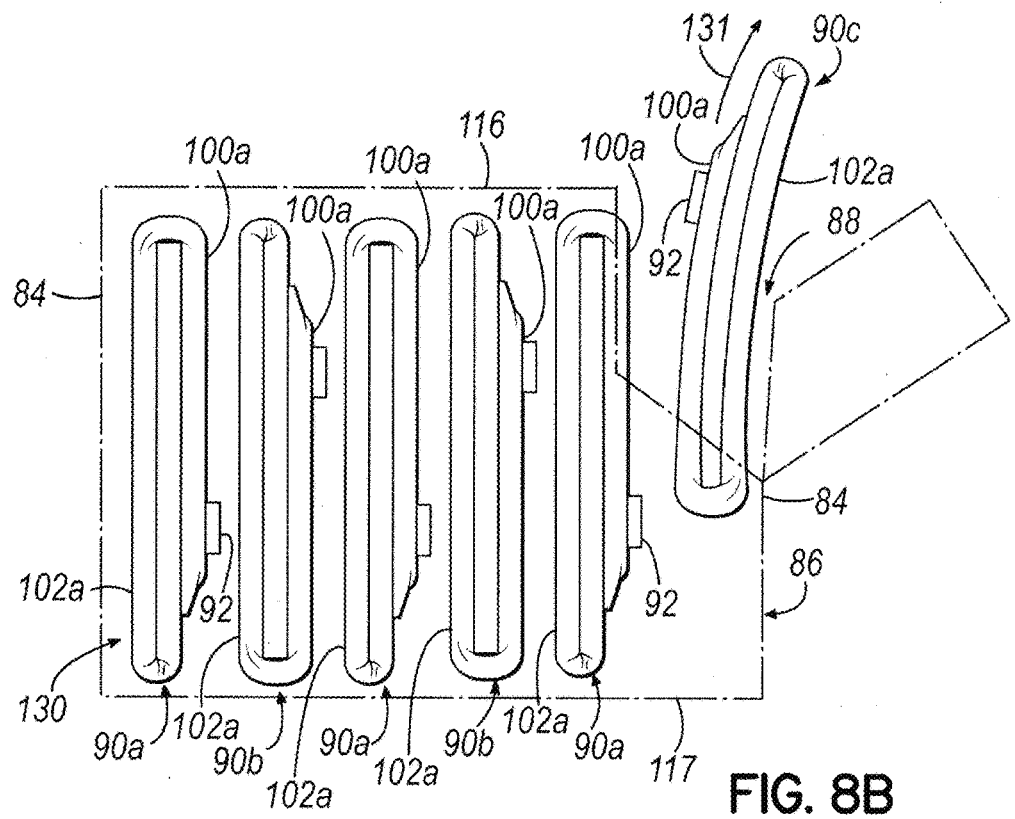
FIG. 8B is a view similar to FIG. 8, schematically illustrating an alternative exemplary stack and one of the products being retrieved therefrom.

With reference to FIG. 8B, in which like reference numerals refer to similar features in the preceding figures, an alternative exemplary stack 130 of disposable absorbent products is illustrated therein. Stack 130 is similar in most respects to stack 115 (FIGS. 8 and 8A) but has a different orientation relative to the opening 88 of packaging enclosure 86. More specifically, in the exemplary orientation of the embodiment of FIG. 8B, retrieval of the folded brief 90c at the end of the stack 130 is such that the rigid component 92 of folded brief 90c follows a path (arrow 131) away from the rigid component 92 of the adjacent folded brief 90a. This contrasts with the embodiment of FIG. 8A, in which retrieval of the folded brief 90c at the end of the stack 115 causes the rigid component 92 of folded brief 90c to follow a path (arrow 119) toward, rather than away from, the rigid component 92 of adjacent folded brief 90a. The embodiment of FIG. 8B may be advantageous in situations in which prevention of contact between adjacent rigid components 92 is desirable.

Figure 9:
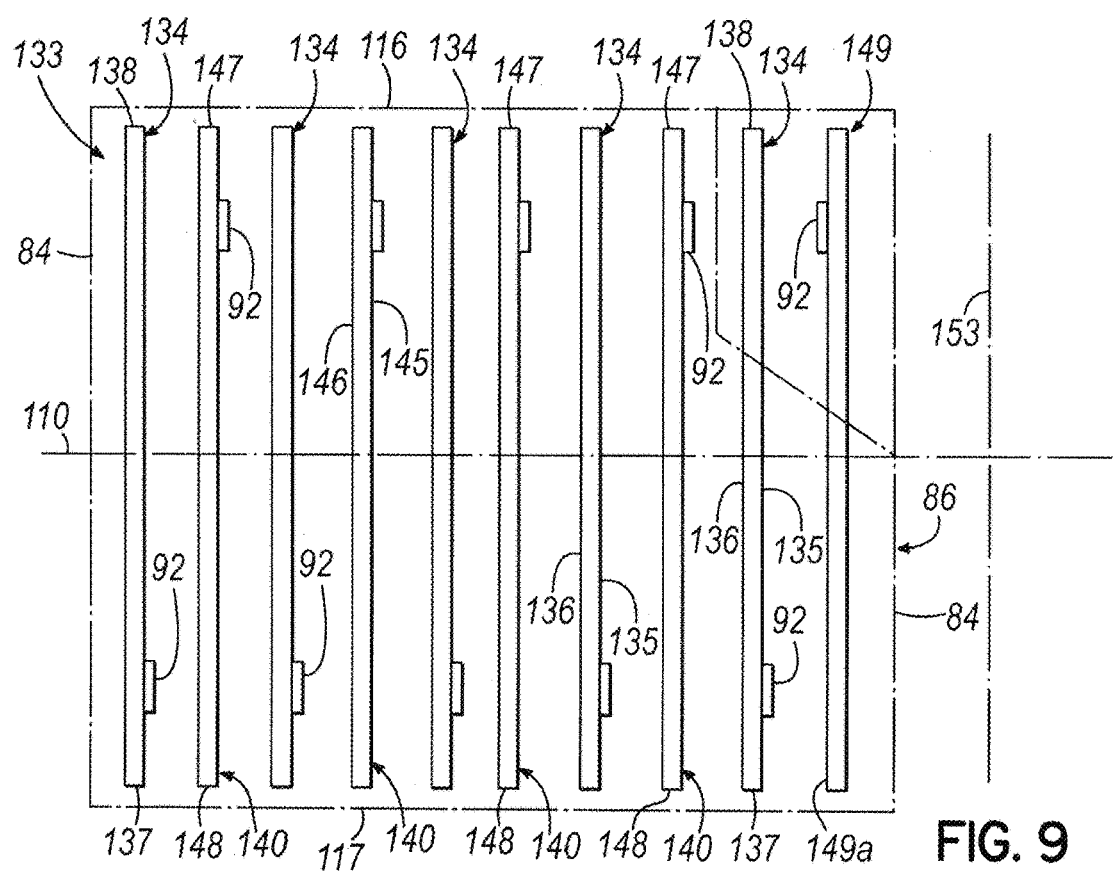
FIG. 9 is a view similar to FIG. 8, schematically illustrating a stack of absorbent products in accordance with another embodiment of the invention.

Referring now to FIG. 9, another embodiment of a stack 133 of disposable absorbent products is illustrated in that figure. For ease of understanding, like reference numerals in FIG. 9 refer to similar features in the preceding figures, the illustration and description of which may be referredto for an understanding of the features of the embodiment of FIG. 9 as well. Stack 133 has a plurality of absorbent products such as disposable diapers or briefs or washable (i.e., not disposable) diapers or briefs that, unlike the preceding embodiments, are substantially unfolded in their stacked configuration. As used herein, the term "substantially unfolded" refers to the absence of a folding (e.g., transverse folding) that divides the absorbent product into two or more panels, but which may nevertheless have relatively small components such as side panels 35, side regions 36, tabs 38a, and/or other types of fastening elements tucked inwardly.

Stack 133 has a first plurality of absorbent products 134 and a second plurality of absorbent products 140, with the absorbent products 134 being oriented upside down i.e., oriented about 180° about stacking axis 110, relative to the absorbent products 140. Each of the absorbent products 134 has respective first and second exterior faces 135, 136, and first and second longitudinal ends 137, 138, while each of the absorbent products 140 has respective first and second exterior faces 145, 146, and first and second longitudinal ends 147, 148. Each of the exemplary absorbent products 134, 140 has a respective rigid component 92, with respective pluralities of wires 94 (not shown) similar to the like-numbered rigid components and wires of the preceding embodiments. Each of the rigid components 92 in the embodiment of FIG. 9 is coupled to one of the exterior faces of the respective absorbent product 134, 140, more specifically in that embodiment, to the respective first exterior faces 135, 145, which may correspond, for example, and without limitation, to the backsheet of a disposable-type absorbent product.

An absorbent product 149 at one end of the stack 133 is oriented, relative to the adjacent absorbent product 134, about 180° about an axis 153 that is perpendicular to the stacking axis 110. In that regard, the absorbent product 149 at the end of the stack 133 is oriented such that the first face 149a of that absorbent product faces the first face 135 of adjacent absorbent product 134. The respective rigid components 92 of the absorbent product 149 at the end of the stack 133 and of the adjacent absorbent product 134 similarly face one another. Further, in that embodiment, the absorbent product 149 is oriented upside down relative to adjacent absorbent product 134. The relative orientation of the absorbent product 149 at the end of the stack 133 provides advantages similar to those described with reference to the preceding embodiments.

With continued reference to FIG. 9, the exemplary arrangement of the absorbent products 134, 140 in stack 133 shares some characteristics with the stacked arrangements in the previous embodiments. For example, the absorbent products 134, 140 alternate in the stack, such that each respective first longitudinal end 137 of an absorbent product 134 is adjacent one or more second longitudinal ends 148 of an absorbent product 140. Further, in the embodiment of FIG. 9, the respective first and second longitudinal ends 137, 148 of adjacent absorbent products 134, 140 lie generally in a common plane, to thereby attain a stable stack, suitable for transfer to a packaging operation and suitable for resting on a flat surface e.g., a store shelf.

From the above disclosure of the general principles of the present invention and the preceding detailed description of exemplary embodiments, those skilled in the art will readily comprehend the various modifications to which this invention is susceptible. Those skilled in the art will similarly readily appreciate that the principles described herein are applicable to uses and methods for manufacturing and/or arranging products associated with the various embodiments. Accordingly, this invention is intended to be limited only by the scope of the following claims and equivalents thereof.

What is claimed is:

1. A stack of folded disposable absorbent products stacked along a stacking axis, wherein each of said folded disposable absorbent products extends longitudinally between a front longitudinal edge and a back longitudinal edge and has a topsheet, a backsheet, and an absorbent core disposed between said topsheet and said backsheet for absorbing fluids secreted by a wearer of said disposable absorbent product, and wherein each said folded disposable absorbent products is folded into at least two panels in which the respective front and back longitudinal edges remain unattached and so as to define first and second edges, in which at least one of said first and second edges is formed by a fold, and front and back oppositely-facing exterior faces, wherein each of the front exterior faces includes identical fastening components, the stack comprising:
a first plurality of said folded disposable absorbent products having respective said front exterior faces facing a common, first direction along the stacking axis; and
at least one of said folded disposable absorbent products having said front exterior face facing a second direction opposite from the first direction along the stacking axis.

2. The stack of claim 1, wherein said at least one of said folded disposable absorbent products is oriented about 180°, about the stacking axis, relative to an adjacent one of said first plurality of said folded disposable absorbent products.

3. The stack of claim 1, further comprising:
a second plurality of said folded disposable absorbent products having respective front exterior faces facing the first direction, and
wherein each first edge of each of said second plurality of said folded disposable absorbent products is adjacent at least one said second edge of said first plurality of said folded disposable absorbent products.

4. The stack of claim 3, wherein said first edges of said first plurality of said folded disposable absorbent products and said second edges of said second plurality of said folded disposable absorbent products lie generally in a common plane.

5. The stack of claim 1, wherein each of said folded disposable absorbent products includes a respective rigid component coupled to said front exterior face or said back exterior face thereof.

6. The stack of claim 5, wherein each of said folded disposable absorbent products includes a respective plurality of wires extending from said rigid component.

7. The stack of claim 5, wherein each of said folded disposable absorbent products is folded into 3 panels, each respective rigid component being located adjacent or at a respective longitudinal end of said respective folded product in an unfolded condition thereof.

8. The stack of claim 1, wherein said at least one of said folded disposable absorbent products is located at one end of the stack.

9. A package of folded disposable absorbent products arranged in a stack, said folded disposable absorbent products being stacked along a stacking axis, wherein each of said folded disposable absorbent products extends longitudinally between a front longitudinal edge and a back longitudinal edge, and wherein each of said folded disposable absorbent products is folded into at least two panels in which the respective front and back longitudinal edges remain unattached and so as to define first and second edges, in which at least one of said first and second edges is formed by a fold, and front and back oppositely-facing exterior faces, wherein each of the front exterior faces includes identical fastening components, the package comprising:
 a first plurality of said folded disposable absorbent products having respective said front exterior faces facing a common, first direction along the stacking axis,
 a second plurality of said folded disposable absorbent products having respective said front exterior faces facing the first direction,
 at least one of said folded disposable absorbent products at an end of said stack having said front exterior face facing a second direction opposite from the first direction along the stacking axis,
 wherein each of said second plurality of said folded disposable absorbent products is oriented about 180°, about the stacking axis, relative to said first plurality of said folded disposable absorbent products.

10. The package of claim 9, wherein each of said folded disposable absorbent products includes a respective rigid component coupled to said front exterior face or said back exterior face thereof.

11. The package of claim 10, wherein each of said folded disposable absorbent products includes a respective plurality of wires extending from said rigid component.

12. A stack of folded absorbent products stacked along a stacking axis, wherein each of said folded absorbent products extends longitudinally between a front longitudinal edge and a back longitudinal edge and has an absorbent core for absorbing fluids secreted by a wearer of said absorbent product, and wherein each of said folded absorbent products is folded into at least two panels in which the respective front and back longitudinal edges remain unattached and so as to define first and second edges, in which at least one of said first and second edges is formed by a fold, and first and second oppositely-facing exterior faces, wherein each of the first exterior faces includes identical fastening components, the stack comprising:
 a first plurality of absorbent products having respective said first exterior faces of said first plurality of said absorbent products facing a common, first direction along the stacking axis; and
 at least one of said folded absorbent products having said first exterior face facing a second direction opposite from the first direction along the stacking axis,
 wherein the second ends of said at least one of said folded absorbent products and said first plurality of said folded absorbent products lie generally in a common plane.

13. The stack of claim 12, wherein each of said folded absorbent products includes a topsheet, and a backsheet in confronting relationship with said topsheet, said absorbent core being disposed between said topsheet and said backsheet.

14. The stack of claim 12, further comprising:
 a second plurality of said folded absorbent products having respective said first exterior faces facing the first direction along the stacking axis.

15. The stack of claim 14, wherein said first ends of said first plurality of said folded absorbent products and said second ends of said second plurality of said folded absorbent products lie generally in a common plane.

16. The stack of claim 12, wherein each of said folded absorbent products includes a respective rigid component coupled to said first exterior face or said second exterior face thereof.

17. The stack of claim 16, wherein each of said folded absorbent products includes a respective plurality of wires extending from said rigid component.

18. The stack of claim 12, wherein said at least one of said absorbent products is located at one end of the stack.

19. The stack of claim 12, wherein each of said absorbent products is folded so as to define at least two panels.

20. A stack of absorbent products stacked along a stacking axis, comprising:
 a plurality of absorbent products, each having first and second oppositely-facing exterior faces;
 a first end absorbent product located at a first end of the stack, said first end absorbent product having first and second oppositely-facing exterior faces and a first rigid component coupled to said first exterior face or second exterior face thereof; and
 a second end absorbent product located at a second end of the stack opposite said first end thereof, said second end absorbent product having first and second oppositely-facing exterior faces and a second rigid component coupled to said first exterior face or second exterior face thereof,
 wherein each of said plurality of absorbent products, said first end absorbent product and said second end absorbent product, have respective absorbent cores for absorbing fluids secreted by a wearer of said respective absorbent product, and
 wherein said first and second end absorbent products are respectively oriented in the stack such that said first and second rigid components face toward a center of the stack.

21. The stack of claim 20, wherein said first and second end absorbent products have respective pluralities of wires extending from said first and second rigid components.

22. The stack of claim 20, wherein each of said plurality of absorbent products, said first end absorbent product, and said second end absorbent product have respective rigid components coupled to said respective first or second exterior faces thereof.

23. The stack of claim 20, wherein each of said at least one absorbent product and said first plurality of absorbent products is folded so as to define at least two panels.

* * * * *